BEST AVAILABLE COPY
Aug 7, 1951 | E. S. BOERNER | Plant Pat. 1,027
ROSE PLANT
Filed May 29, 1950
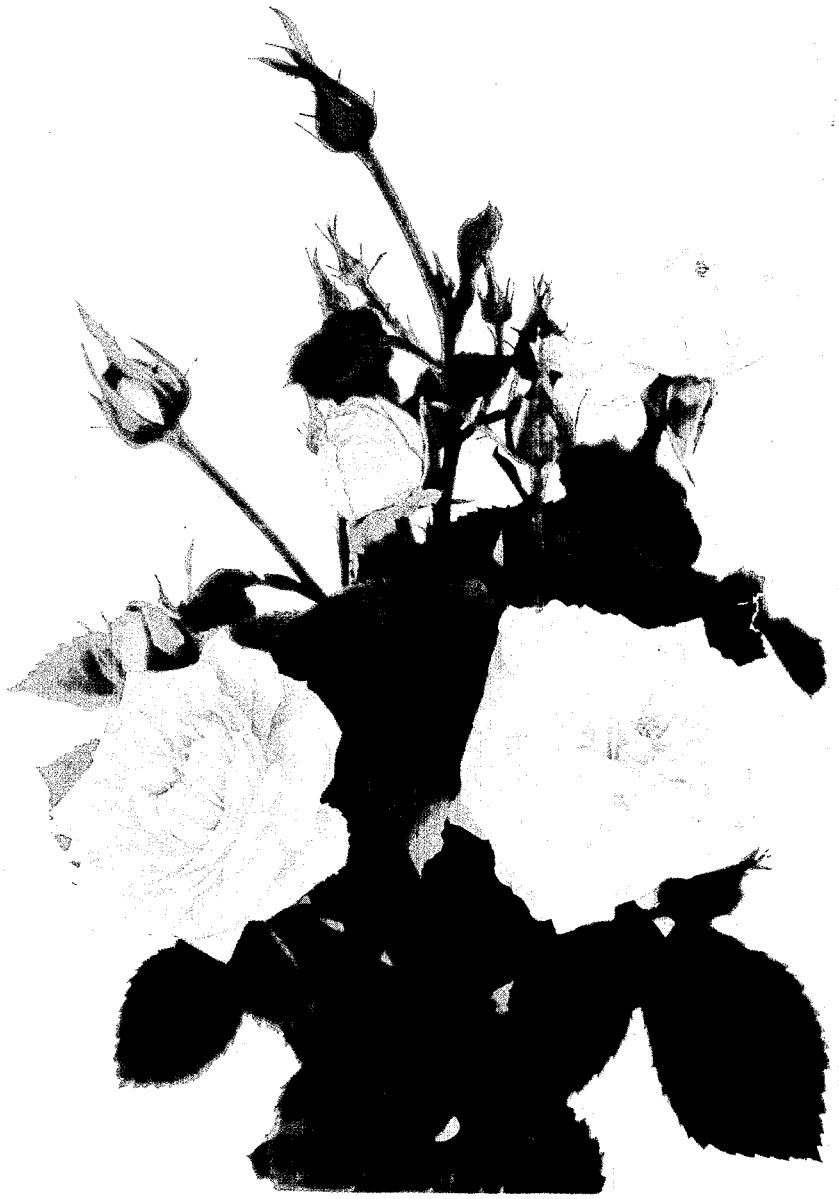
Inventor
E. S. Boerner
By: Robbs Robb
Attorneys.

Patented Aug. 7, 1951

Plant Pat. 1,027

BEST AVAILABLE COPY

UNITED STATES PATENT OFFICE 1,027

ROSE PLANT

Eugene S. Boerner, Newark, N. Y., assignor to Jackson & Perkins Company, Newark, N. Y., a corporation of New York Application May 29, 1950, Serial No. 164,899

1 Claim. (Cl. 47—61)

The present invention relates to a new and distinct variety of rose plant of the polyantha class, originated by crossing the varieties "Goldilocks" (Plant Patent No. 672) × "Marionette" (Plant Patent No. 569).

The primary objective in making this cross was to get a direct descendant of the original "Pinocchio" (Plant Patent No. 484), without the yellow color which is the characteristic color of the parent varieties. This objective was obtained in another plant, and one of the fellow seedlings appeared as this light pink, with a vigorous and free-growing plant, producing a shower of blooms over the whole plant when it first blooms in the spring.

The plants of the new variety differ from "Pinocchio" in that the original flower clusters are not quite so large, but many more branches are formed, while the blooming and repeating habits are similar to those of other members of the "Pinocchio" family.

Other outstanding and desirable features of the new variety which distinguish it from its parents as well as from other varieties are evidenced by the following:

(1) The mound-like habit of growth;

(2) The hundreds of blooms which appear and last for a long period;

(3) The Shrimp Pink lightly overcast with La France Pink color of the blooms, which is different from the characteristic "Pinocchio" pink which is the nearest comparable variety; and (4) Its freedom of winter forcing when used as a pot rose.

Asexual reproduction of this new variety by budding at Newark, New York, and at Pleasanton, California, shows that the foregoing characteristics come true to form and are established and transmitted through succeeding propagations.

The accompanying drawing shows specimens of the new variety, with the flowers and foliage in different stages of development.

The following is a detailed description of the new variety, with color terminology in accordance with Ridgway's Color Standards and Nomenclature:

Parentage: Seedling.

*Seed parent.*—"Goldilocks."

*Pollen parent.*—"Marionette."

Classification:

*Botanic.*—Polyantha.

*Commercial.*—Floribunda.

*Flower*

(Observations made from pot plants in the greenhouse at Newark, New York, in the month of March, 1950).

Blooming habit: Recurrent—continuous.

Bud:

*Size.*—Medium.

*Form.*—Ovoid. Is not affected by wet or hot weather.

*Color.*—When sepals first divide—Begonia Rose, Plate 1. When petals begin to unfurl—Eosine Pink, Plate 1. When half blown—inside of petals—Shrimp Pink, Plate 1, overcast with La France Pink, Plate 1; reverse of petals—Pale Flesh Color, Plate 14, lightly overcast with La France Pink, Plate 1.

*Sepals.*—Serrated; slightly branched; "hood" above bud. Curl back when petals begin to unfurl. Color—inside: Biscay Green, Plate 17; outside: Bice Green, plate 17.

*Calyx.*—Shape—funnel. Size—small. Aspect—smooth. Odor when rubbed—none. Color—Rinnemann's Green, Plate 18.

*Peduncle.*—Length—short. Aspect—smooth. Color—Parrot Green, Plate 6. Strength—erect; slender.

*Opening.*—Bud opens up well. Is not affected by adverse weather conditions.

Bloom:

*Size.*—Medium. Average size when fully expanded, 3½ inches.

*Borne.*—Singly and in irregular clusters, making the plant appear as a mound in the spring bloom.

*Stems.*—Medium length; normal strength.

*Form.*—When first open—flat. Permanence—retains its form to the end.

*Petalage.*—Very double (many petals and stamens hidden). Number of petals under normal conditions, 50 to 60.

*Color.*—Center of flower—La France Pink, Plate 1. Outer petals—Shrimp Pink, Plate 1. Base of petals—Chalcedony Yellow, Plate 17. Inside of petals—Shrimp Pink, Plate 1, lightly overcast with La France Pink, Plate 1. Reverse of petals—Shrimp Pink, Plate 1. General tonality from a distance—Shrimp Pink, Plate 1, lightly overcast with La France Pink, Plate 1.

BEST AVAILABLE COPY

*Discoloration.*—General tonality at end of first day—La France Pink, Plate 1. Second day—Shrimp Pink, Plate 1, lightly overcast with La France Pink, Plate 1. Third day—Shrimp Pink, Plate 1.

Petals:

*Texture.*—Thin. Are not affected by wet or hot weather.

*Appearance.*—Inside—shiny. Outside—shiny.

*Form.*—Oval.

*Arrangement.*—Imbricated (regularly arranged shingle-like). Petaloids in center—few and small.

*Persistence.*—Drop off cleanly.

*Fragrance.*—Moderate. Nature—tea (average hybrid tea scent).

*Lasting quality.*—On the plant and as a cut flower—long.

Genital organs:

*Stamens, anthers.*—Small size; few. Color—Orange Buff, Plate 3. Arrangement—regular around styles.

*Stamens, filaments (threads).*—Short. Color—Barium Yellow, Plate 16.

*Pollen.*—Color—Naphthalene Yellow, Plate 16.

*Styles.*—Loosely separated and of uneven length. Long and thin.

*Stigmas.*—Color—Sea-foam Yellow, Plate 31.

*Ovaries.*—All enclosed in calyx.

*Plant*

Form: Bush.

Growth: Vigorous, branching.

Foliage: 3 to 5 leaflets.

*Size.*—Medium.

*Quantity.*—Normal.

*Color.*—New foliage—upper side—Oil Green, Plate 5; under side—Courge Green, Plate 17. Old foliage—upper side—Forest Green, Plate 17; under side—Light Bice Green, Plate 17.

*Shape.*—Oval pointed.

*Texture.*—Upper side—smooth. Under side—smooth. Ribs and veins—ordinary.

*Edge.*—Serrated (saw toothed).

*Serration.*—Double; small.

*Leaf stem.*—Color—Courge Green, Plate 17. Under side—smooth.

*Stipules.*—Medium length and smooth.

*Disease resistance.*—Resistant.

Wood:

*New wood.*—Color—Parrot Green, Plate 6. Bark—smooth.

*Old wood.*—Color—Jade Green, Plate 31. Bark—smooth.

Thorns:

*Quantity.*—On main stalks from base and on laterals from stalk—ordinary.

*Form.*—Narrow base. Medium length and straight.

*Color when young.*—Eugenia Red, Plate 13.

*Position.*—Irregular.

*Prickles.*—Quantity on main stalks and on laterals—none.

*Short needles.*—Quantity on main stalks and on laterals—none.

I claim:

A new and distinct variety of rose plant of the polyantha class, characterized as to novelty by its mound-like, vigorous and free-growing habits of growth, by its profusion of long-lasting blooms of Shrimp Pink color lightly overcast with La France Pink, and by its freedom of winter forcing when used as a pot rose, substantially as shown and described.

EUGENE S. BOERNER.

No references cited.